(12) United States Patent
Iggulden

(10) Patent No.: US 6,360,613 B1
(45) Date of Patent: Mar. 26, 2002

(54) CONTAINER AND TESTING DEVICE FOR SPORT BALLS

(76) Inventor: Jerry Iggulden, c/o Blakely, Sokoloff, Taylor & Zafman, LLP, 12400 Wilshire Blvd., Suite 700, Los Angeles, CA (US) 90025

(*) Notice: Subject to any disclaimer, the term of this patent is extended or adjusted under 35 U.S.C. 154(b) by 0 days.

(21) Appl. No.: 09/574,549

(22) Filed: May 18, 2000

(51) Int. Cl.⁷ .................................................. G01N 3/08
(52) U.S. Cl. .......................................... 73/820; 73/824
(58) Field of Search .......................... 73/818, 820, 824

(56) References Cited

U.S. PATENT DOCUMENTS

| | | | | |
|---|---|---|---|---|
| 3,665,757 A | * | 5/1972 | Hong | 73/818 |
| 3,987,699 A | * | 10/1976 | Popenoe | 411/13 |
| 4,154,095 A | * | 5/1979 | Snyder | 73/744 |
| 5,222,391 A | | 6/1993 | Reenstra | |
| 5,245,862 A | | 9/1993 | Zeiss | |
| 5,291,774 A | | 3/1994 | Putnam, Jr. | |
| 5,511,410 A | | 4/1996 | Sherts | |
| 5,567,870 A | | 10/1996 | Harris | |
| 5,639,969 A | | 6/1997 | D'Adamo | |
| 5,760,312 A | | 6/1998 | MacKay et al. | |

FOREIGN PATENT DOCUMENTS

GB           230250           3/1925

* cited by examiner

*Primary Examiner*—Max Noori
(74) *Attorney, Agent, or Firm*—Blakely, Sokoloff, Taylor & Zafman LLP

(57) ABSTRACT

A container for storing sport balls incorporates a device for testing the playing condition of the balls. A cylindrical container has a removable end cap that may be attached to the closed end of the container. A ball placed within the end cap is subjected to predetermined compression when the end cap is secured onto the container. A pressure indicator in the end cap provides a visual indication of the internal pressure in the ball, and hence, one important measure of the playing condition of the ball.

7 Claims, 1 Drawing Sheet

CONTAINER AND TESTING DEVICE FOR SPORT BALLS

BACKGROUND OF THE INVENTION

1. Field of the Invention

This invention relates generally to the field of sport balls, such as tennis balls. More particularly, the invention comprises the combination of a container for a plurality of sport balls with a device for testing the playing condition of the balls.

2. Background

Tennis balls and certain other types of sport balls, such as racquet balls and handballs, are manufactured with a predetermined internal pressure, which imparts resiliency. The pressure is retained within a sphere of elastomeric material; however, the material is not perfectly impermeable. The internal pressure diminishes over time and with extended play. As the pressure diminishes, so does the resiliency of the ball, which has a deleterious effect on the playing characteristics of the ball.

Official organizations for tennis and other sports have established specifications for the balls used to play the respective sports. For example, the International Tennis Federation (ITF) Rules of Tennis specify that the ball shall have a bound of more than 53 inches and less than 58 inches when dropped 100 inches upon a concrete base. The Rules also specify that the forward and return deformation of the ball when placed under a load of 18 pounds shall be between 0.220 inch and 0.290 inch. Both of these specifications relate to the resiliency of the ball and hence to its playing characteristics. Recreational players are generally not concerned with whether or not a particular ball meets the precise specifications of an official organization. Such players are more concerned with the general playability of a ball and will often test a ball by squeezing it by hand or bouncing it on pavement. These informal tests are highly subjective. A number of devices have been proposed for objectively testing sport balls, particularly tennis balls. Such devices are shown, for example, in U.S. Pat. Nos. 5,222,391; 5,245,862; 5,291,774; 5,511,410; 5,567,870; 5,639,969; and 5,760,312.

Some of the prior art testing devices shown in the above-mentioned patents are intended for laboratory use, while others are intended to be used by individual players. However, all of the known prior art devices are relatively complex and, therefore, relatively expensive. Many of the devices have electronic components and all have one or more moving parts. There remains a perceived need for an inexpensive ball tester that can be provided to consumers at the time that the balls are purchased, analogous to the way that many dry cell batteries are sold with integral devices for testing the condition of the battery. Preferably, such a device would be simple to use and would be incorporated into the package in which balls are sold and stored so that the player would not be burdened with the inconvenience and weight of an additional item to carry.

SUMMARY OF THE INVENTION

The present invention provides a device for testing the playing condition of sport balls. The invention is preferably configured as the testing device in combination with a container for storing the sport balls; however, the invention may also be configured as a stand-alone testing device. A cylindrical container for the sport balls has a removable end cap that may be attached to the closed end of the container. A ball placed within the end cap is subjected to predetermined compression when the end cap is secured onto the container. A pressure indicator in the end cap provides a visual indication of the internal pressure in the ball, and hence, one important measure of the playing condition of the ball.

DETAILED DESCRIPTION OF THE INVENTION

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

Figure 1:
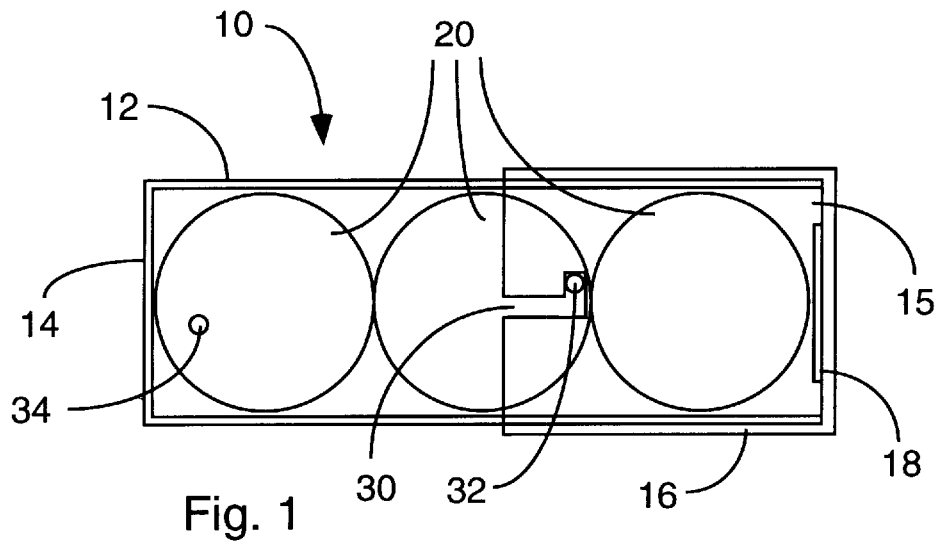
FIG. 1 is a side view of a combination container and tester in accordance with the present invention.

FIG. 1 illustrates a combination ball container and tester 10 in accordance with the present invention. Container/tester 10 comprises a cylindrical tube 12 closed at end 14 and a cap 16. In the case of a device for tennis balls, cylindrical tube 12 is preferably dimensioned to house three balls 20 as is customary. Cylindrical tube 12 is preferably made of a clear plastic material, such as PETE, of sufficient strength to maintain internal pressurization sufficient for extended storage of balls 20 prior to use. A pressure seal (not shown) is provided at end 15 of tube 12 under cap 16. The pressure seal is removed and discarded by the consumer when balls 20 are first used.

Cap 16 preferably includes a plurality of L-shaped slots 30 which cooperate with protrusions 32 on cylindrical tube 12 to provide a bayonet-type fitting to retain cap 16 in place. Slots 30 may have a spiral configuration to provide a mechanical advantage when securing cap 16 in place. Alternatively, tube 12 and cap 16 may have cooperating screw threads instead of a bayonet-type fitting. Cap 16 allows container/tester 10 to be used for conveniently storing and transporting balls 20 even after the pressure seal has been removed from tube 12. Cap 16 is preferably made of a clear plastic material, but is preferably somewhat more rigid than tube 12. Thus, cap 16 may be made of styrene, polycarbonate or similar material.

Figure 2:
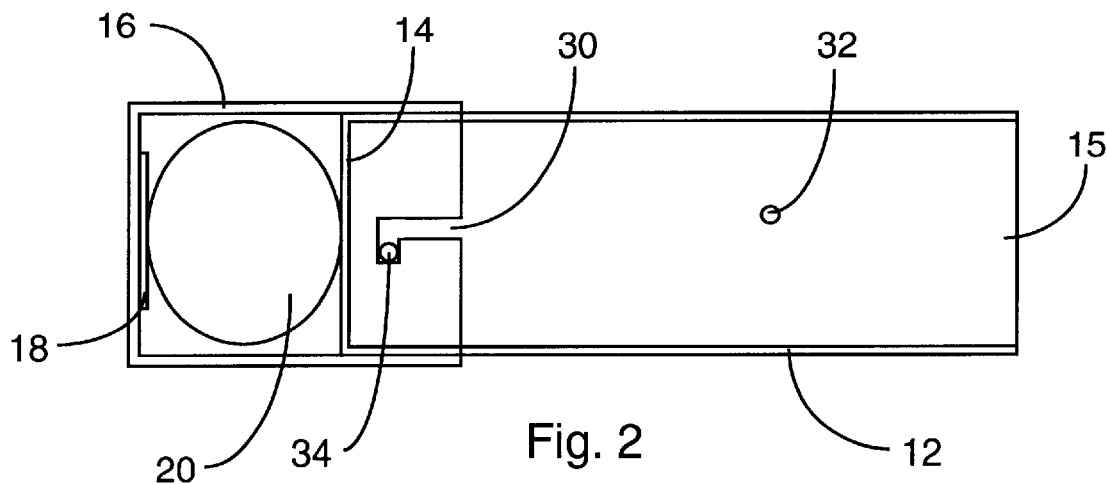
FIG. 2 is a side view of the apparatus of FIG. 1 in a ball-testing configuration.

Referring now to FIG. 2, a ball 20 is shown being tested for playing condition. The ball is placed inside cap 16 and the cap is secured over closed end 14 of tube 12 with slots 30 engaging protrusions 34. Protrusions 34 are spaced from end wall 14 so that ball 20 is slightly compressed when cap 16 is secured in place. As explained above, ITF specifications call for a forward deformation of more than 0.220 inch and less than 0.290 inch under a load of 18 pounds. Thus, if the dimensions are selected so that cap 16 compresses ball 20 by an amount in the specified range, a ball in new condition will exert a force of approximately 18 pounds against cap 16. In order to ascertain the playing condition of the ball, it is simply necessary to obtain an approximate measure of the force exerted against cap 16. Any suitable force indicator may be used, such as, for example, a springoperated indicator or an electronic display coupled to a pressure transducer.

In one preferred embodiment, an indicator 18 is attached to the inside of cap 16. Indicator 18 comprises an opaque fluid enclosed within a pouch of flexible plastic. An indicator of this type is disclosed in U.S. Pat. No. 3,987,699, the disclosure of which is incorporated herein by reference. When the fluid within indicator 18 is displaced as a result of pressure exerted against indicator 18 by compressed ball 20, a visual indication of the displacement is provided. For example, the fluid may be a dark color, which in the absence of pressure completely obscures an underlying color on one wall of the pouch. When the thickness of the fluid is sufficiently reduced, the underlying color shows through. The degree to which the underlying color appears is directly related to the pressure exerted against indicator 18 and thereby provides a visual indication of the playing condition of ball 20.

Figure 3:
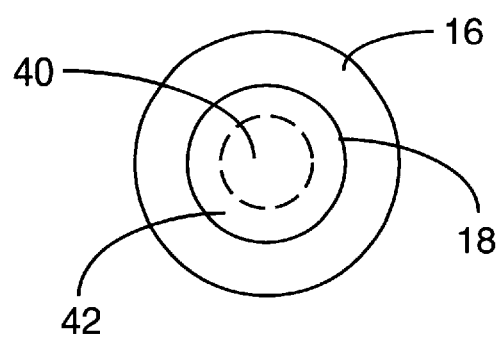
FIG. 3 is an end view of the testing device showing the ball condition indicator.

FIG. 3 is an end view of cap 16, through which indicator 18 may be viewed. A ball in good playing condition will exert sufficient force against indicator 18 to displace the fluid therein within a central region 40. Region 40 will thus have a different hue from surrounding region 42. A ball in poorer playing condition will exert less force against indicator 18 and the color differentiation between regions 40 and 42 will be diminished. In addition, the diameter of central region 40 will appear reduced. A ball in very poor condition will exert insufficient force against indicator 18 to displace the fluid and the entire face of indicator 18 will appear as a solid hue.

It will be recognized that the above described invention may be embodied in other specific forms without departing from the spirit or essential characteristics of the disclosure. Thus, it is understood that the invention is not to be limited by the foregoing illustrative details, but rather is to be defined by the appended claims.

What is claimed is:

1. A device for testing playing condition of a sport ball comprising:
   a cylindrical container having an end wall defining a first chamber on a first side of the end wall for storing at least one sport ball;
   a cap for mating engagement with the container so as to form a second chamber on a second side of the end wall having an axial dimension sufficiently small to partially compress a sport ball disposed therein; and
   an indicator to provide a visual indication of a force exerted in the axial direction by the partially compressed sport ball.

2. The device of claim 1 wherein the sport ball is a tennis ball.

3. The device of claim 1 wherein the cap engages with the container with a bayonet-type fitting.

4. The device of claim 3 wherein the cap also engages with an end of the container opposite the end wall.

5. The device of claim 1 wherein the indicator comprises an indicator fluid contained in a flexible pouch.

6. The device of claim 5 wherein the indicator fluid is colored.

7. The device of claim 6 wherein the visual indication comprises a change in color hue.

* * * * *

UNITED STATES PATENT AND TRADEMARK OFFICE
CERTIFICATE OF CORRECTION

PATENT NO. : 6,360,613 B1
DATED : March 26, 2002
INVENTOR(S) : Iggulden

It is certified that error appears in the above-identified patent and that said Letters Patent is hereby corrected as shown below:

<u>Title page,</u>
Item [56], References Cited, U.S. PATENT DOCUMENTS, please delete "Hong" and insert -- Hoag --.

Signed and Sealed this

Seventh Day of September, 2004

JON W. DUDAS
*Director of the United States Patent and Trademark Office*